United States Patent
Haramura et al.

(10) Patent No.: US 7,456,022 B2
(45) Date of Patent: Nov. 25, 2008

(54) SOLID SUPPORT HAVING LIGAND IMMOBILIZED THEREON BY USING PHOTOCLEAVABLE LINKER

(75) Inventors: Masayuki Haramura, Kamakura (JP); Akito Tanaka, Tsukuba (JP)

(73) Assignee: Reverse Proteomics Research Institute Co., Ltd., Tokyo (JP)

( * ) Notice: Subject to any disclaimer, the term of this patent is extended or adjusted under 35 U.S.C. 154(b) by 0 days.

(21) Appl. No.: 11/572,972

(22) PCT Filed: Jul. 28, 2005

(86) PCT No.: PCT/JP2005/014266

§ 371 (c)(1),
(2), (4) Date: Mar. 7, 2007

(87) PCT Pub. No.: WO2006/011673

PCT Pub. Date: Feb. 2, 2006

(65) Prior Publication Data

US 2007/0212731 A1    Sep. 13, 2007

(30) Foreign Application Priority Data

Jul. 30, 2004    (JP) .............................. 2004-224634

(51) Int. Cl.
B01J 20/26    (2006.01)
G01N 33/547    (2006.01)

(52) U.S. Cl. ............................ 436/136; 436/6; 435/7.1; 435/287.2

(58) Field of Classification Search ................. 436/136, 436/6; 536/23.1; 435/7.1, 287.2
See application file for complete search history.

(56) References Cited

U.S. PATENT DOCUMENTS 6,057,096 A * 5/2000 Rothschild et al. ............. 435/6
6,465,628 B1 * 10/2002 Ravikumar et al. ........ 536/23.1
2002/0168644 A1   11/2002 Aebersold et al.
2003/0027140 A1    2/2003 Ju et al.
2004/0265810 A1   12/2004 Aebersold et al.

FOREIGN PATENT DOCUMENTS

WO    WO 02/079519 A1    10/2002
WO    WO 02/093131 A2    11/2002

OTHER PUBLICATIONS

Gygi, Steven P. et al., Quantitative analysis of complex protein mixtures using isotope-coded affinity tags. Oct. 1999, Nature Biotechnology, vol. 17, pp. 994-999.*
Cano et al., *J. Org. Chem*, 67(1): 129-135 (2002).
Enders et al., *Tetrahedron Letters*, 45: 2839-2841 (2004).
Holmes et al., *J. Org. Chem.*, 60(8): 2318-2319 (1995).
Horton et al., *Tetrahedron Letters*, 41: 9181-9184 (2000).
Kessler et al., *Organic Letters*, 5(8): 1179-1181 (2003).
Tamura et al., *Bioconjugate Chem.*, 14(6): 1222-1230 (2003).

* cited by examiner

*Primary Examiner*—Jill Warden
*Assistant Examiner*—Christine T Mui
(74) *Attorney, Agent, or Firm*—Leydig, Voit & Mayer, Ltd.

(57) ABSTRACT

The present invention provides a method of analyzing the interaction between a ligand and a target molecule, which uses a solid support wherein the ligand is immobilized via a linker cleavable by photoirradiation, particularly a method of searching and purifying a target molecule. By intervening a linker specifically cleavable by photoirradiation between the ligand molecule and the solid support, release and elution of the target molecule from the solid support without using a ligand or salt at a high concentration can be enabled, and suppression of release and elution of a nonspecific protein can be enabled.

8 Claims, 2 Drawing Sheets

SOLID SUPPORT HAVING LIGAND IMMOBILIZED THEREON BY USING PHOTOCLEAVABLE LINKER

TECHNICAL FIELD

The present invention relates to a solid support having a ligand immobilized thereon. More particularly, the present invention relates to a solid support having a ligand immobilized thereon wherein a ligand is immobilized via a linker, preparation thereof, and use thereof.

BACKGROUND ART

A protein can be investigated from various aspects with high precision when the protein purified to a purity based on a three-dimensional structure can be obtained. In general, however, a large amount of labor is necessary for purification of protein to such level. Particularly, a highly pure protein, which is rich in active conformation, not only having a high purity on an SDS gel (purity based on a primary structure), but also having a high purity based on a three-dimensional structure is extremely difficult to obtain. As a method meeting this object, purification using an affinity resin with an immobilized ligand having a specific binding ability has been employed. In the prior art, however, a ligand compound or salt is used at a high concentration to release and elute out a protein bound to a ligand on a resin. When a low-molecular-weight compound such as a pharmaceutical product and the like is used as a ligand, since solubility thereof in water is generally insufficient, a solution having a sufficient concentration to release the protein often cannot be prepared. Even when a high concentration ligand solution could be prepared, denaturation of protein due to the high concentration of ligand is problematic. Moreover, even when a high concentration salt is used, since the function is theoretically based on the antagonism to a nonspecific hydrogen bond due to the high concentration salt, it is necessary to add a salt at so high a concentration as to forcibly disrupt a stable ligand-protein complex structure under specific binding. In this case, a problem of denaturation of protein occurs, which is caused by simultaneous cleavage of a hydrogen bond necessary for maintaining the three-dimensional structure of the protein.

It is an object of the present invention to provide a method that enables selective purification of a protein to a high purity. More specifically, the present invention aims at providing a technique that enables, without using a high concentration ligand compound and salt, release and elution of a protein from an affinity resin.

DISCLOSURE OF THE INVENTION

With such background situation, the present inventors have studied in an attempt to establish a new technique that enables, without utilizing a high concentration ligand compound and salt, release and elution of a protein from an affinity resin, based on the fundamental technology relating to the high affinity resin developed by the present inventors. As a result, they have succeeded in the development of a novel purification method of a high purity protein, which satisfies the object, by allowing a linker specifically cleavable by the light to intervene between a ligand molecule and a resin solid support.

When a protein mixture containing a protein other than a protein selectively bound to a ligand is treated with an affinity resin with an immobilized ligand, a selective binding protein bound to the ligand and a nonspecific binding protein bound to a part other than the ligand are present on the affinity resin. By a conventional elution method including elution with a high concentration salt, a surfactant that denatures protein to cause elution thereof and the like, a selective binding protein and a nonselective protein are simultaneously eluted, where elution and recovery of the selective binding protein alone is difficult. The present inventors have developed a new method capable of eluting and recovering a selective binding protein alone by allowing a linker specifically cleavable by photoirradiation to intervene between a ligand molecule and a resin solid support.

Accordingly, the present invention provides the following.

[1] A solid support for the analysis of a specific interaction between a ligand and a target molecule, wherein the ligand is immobilized via a linker cleavable by photoirradiation.

[2] The solid support of the above-mentioned [1], which is used for searching a target molecule.

[3] The solid support of the above-mentioned [1], which is used for purifying a target molecule.

[4] The solid support of any one of the above-mentioned [1] to [3], which is represented by the following formula (I) or (II):

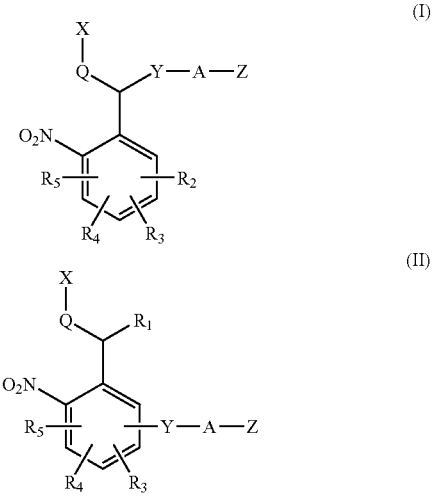

wherein X is a ligand, which is cleavable by photoirradiation; Y is a single bond or an optionally substituted alkylene group; A is a group usable for binding to a solid support; Z is a solid support; Q is NH, O or S; $R_1$ is a hydrogen atom, an optionally substituted alkyl group or an optionally substituted aryl group; $R_2$ is a hydrogen atom, an optionally substituted alkyl group, an optionally substituted aryl group, an optionally substituted alkoxy group, a halogen atom or a cyano group; $R_3$ is a hydrogen atom, an optionally substituted alkyl group, an optionally substituted aryl group, an optionally substituted alkoxy group, a halogen atom or a cyano group; $R_4$ is a hydrogen atom, an optionally substituted alkyl group, an optionally substituted aryl group, an optionally substituted alkoxy group, a halogen atom or a cyano group; and $R_5$ is a hydrogen atom, an optionally substituted alkyl group, an optionally substituted aryl group, an optionally substituted alkoxy group, a halogen atom or a cyano group.

[5] The solid support of the above-mentioned [4], wherein $R_2$ is a hydrogen atom, an optionally substituted alkyl group or a optionally substituted alkoxy group; $R_3$ is a hydrogen atom, an optionally substituted alkyl group or an optionally substituted alkoxy group; $R_4$ is a hydrogen atom, an optionally substituted alkyl group or an optionally substituted alkoxy group; and $R_5$ is a hydrogen atom, an optionally substituted alkyl group or an optionally substituted alkoxy group.

[6] The solid support of the above-mentioned [4], which is represented by the following formula:

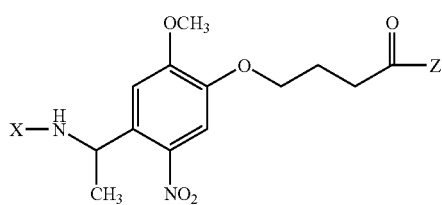

wherein each symbol is as defined above.

[7] A compound represented by the following formula (I') or (II'):

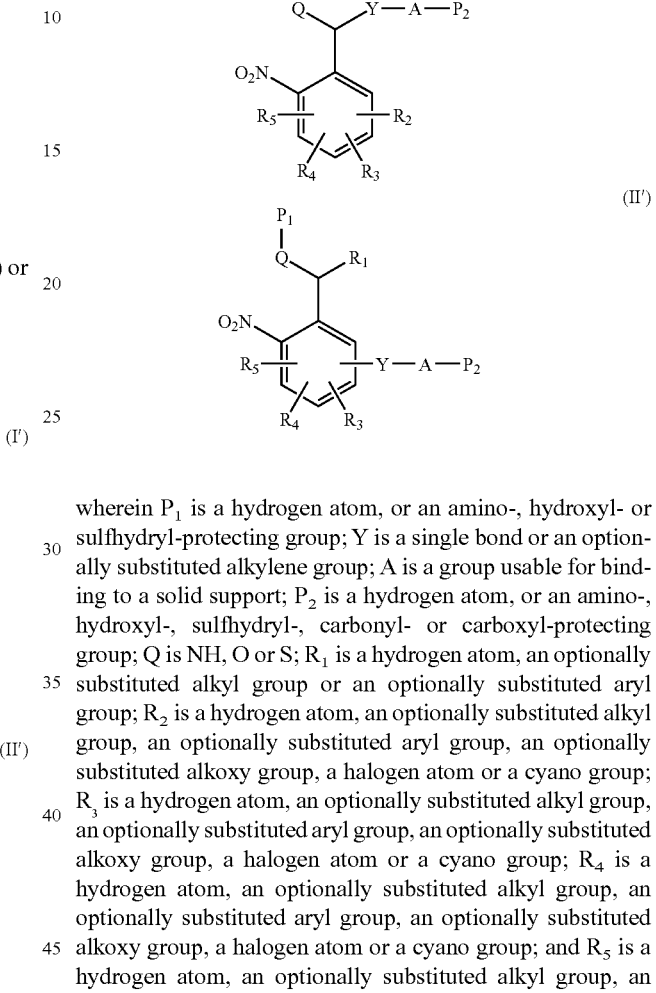

wherein $P_1$ is a hydrogen atom, or an amino-, hydroxyl- or sulfhydryl-protecting group; Y is a single bond or an optionally substituted alkylene group; A is a group usable for binding to a solid support; $P_2$ is a hydrogen atom, or an amino-, hydroxyl-, sulfhydryl-, carbonyl- or carboxyl-protecting group; Q is NH, O or S; $R_1$ is a hydrogen atom, an optionally substituted alkyl group or an optionally substituted aryl group; $R_2$ is a hydrogen atom, an optionally substituted alkyl group, an optionally substituted aryl group, an optionally substituted alkoxy group, a halogen atom or a cyano group; $R_3$ is a hydrogen atom, an optionally substituted alkyl group, an optionally substituted aryl group, an optionally substituted alkoxy group, a halogen atom or a cyano group; $R_4$ is a hydrogen atom, an optionally substituted alkyl group, an optionally substituted aryl group, an optionally substituted alkoxy group, a halogen atom or a cyano group; and $R_5$ is a hydrogen atom, an optionally substituted alkyl group, an optionally substituted aryl group, an optionally substituted alkoxy group, a halogen atom or a cyano group.

[8] A linker used for immobilizing a ligand on a solid support, which is represented by the following formula (I') or (II'):

wherein $P_1$ is a hydrogen atom, or an amino-, hydroxyl- or sulfhydryl-protecting group; Y is a single bond or an optionally substituted alkylene group; A is a group usable for binding to a solid support; $P_2$ is a hydrogen atom, or an amino-, hydroxyl-, sulfhydryl-, carbonyl- or carboxyl-protecting group; Q is NH, O or S; $R_1$ is a hydrogen atom, an optionally substituted alkyl group or an optionally substituted aryl group; $R_2$ is a hydrogen atom, an optionally substituted alkyl group, an optionally substituted aryl group, an optionally substituted alkoxy group, a halogen atom or a cyano group; $R_3$ is a hydrogen atom, an optionally substituted alkyl group, an optionally substituted aryl group, an optionally substituted alkoxy group, a halogen atom or a cyano group; $R_4$ is a hydrogen atom, an optionally substituted alkyl group, an optionally substituted aryl group, an optionally substituted alkoxy group, a halogen atom or a cyano group; and $R_5$ is a hydrogen atom, an optionally substituted alkyl group, an optionally substituted aryl group, an optionally substituted alkoxy group, a halogen atom or a cyano group.

[9] The linker of the above-mentioned [8], which is cleavable by photoirradiation.

[10] A solid support for the analysis of a specific interaction between a ligand and a target molecule, wherein the ligand is immobilized via a linker of the above-mentioned [9].

[11] A method of searching a target molecule, which comprises (1) a step of immobilizing a ligand on a solid support via a linker cleavable by photoirradiation, (2) a step of mixing a solid support with the ligand immobilized thereon, which is obtained in the above-mentioned (1), and a sample wherein a target molecule of the ligand is or is not contained, (3) a step of cleaving a ligand from the solid support by irradiation of light, and (4) a step of confirming binding of the target molecule to the ligand.

[12] The method of the above-mentioned [11], wherein the solid support with a ligand immobilized thereon is represented by the following formula (I) or (II):

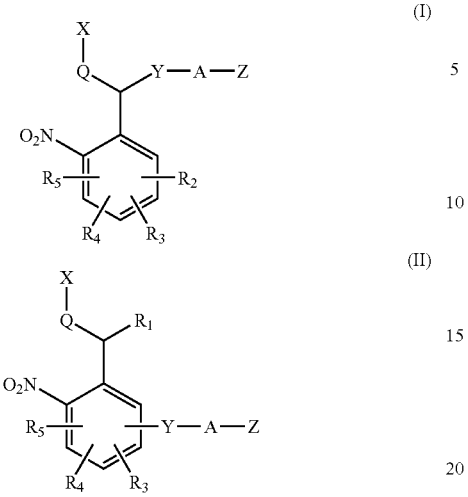

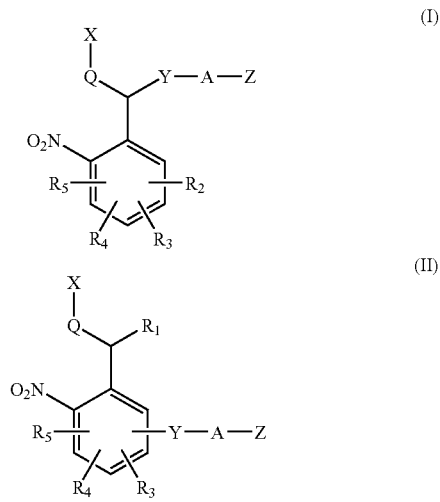

wherein X is a ligand, which is cleavable by photoirradiation; Y is a single bond or an optionally substituted alkylene group; A is a group usable for binding to a solid support; Z is a solid support; Q is NH, O or S; $R_1$ is a hydrogen atom, an optionally substituted alkyl group or an optionally substituted aryl group; $R_2$ is a hydrogen atom, an optionally substituted alkyl group, an optionally substituted aryl group, an optionally substituted alkoxy group, a halogen atom or a cyano group; $R_3$ is a hydrogen atom, an optionally substituted alkyl group, an optionally substituted aryl group, an optionally substituted alkoxy group, a halogen atom or a cyano group; $R_4$ is a hydrogen atom, an optionally substituted alkyl group, an optionally substituted aryl group, an optionally substituted alkoxy group, a halogen atom or a cyano group; and $R_5$ is a hydrogen atom, an optionally substituted alkyl group, an optionally substituted aryl group, an optionally substituted alkoxy group, a halogen atom or a cyano group.

[13] The method of the above-mentioned [12], wherein $R_2$ is a hydrogen atom, an optionally substituted alkyl group or an optionally substituted alkoxy group; $R_3$ is a hydrogen atom, an optionally substituted alkyl group or an optionally substituted alkoxy group; $R_4$ is a hydrogen atom, an optionally substituted alkyl group or an optionally substituted alkoxy group; and $R_5$ is a hydrogen atom, an optionally substituted alkyl group or an optionally substituted alkoxy group.

[14] The method of the above-mentioned [12], wherein the solid support is represented by the following formula:

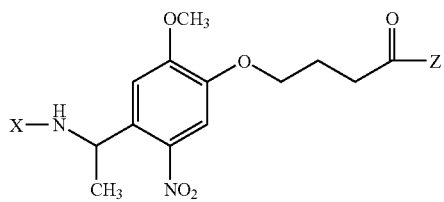

wherein each symbol is as defined above.

[15] A method of purifying a target molecule, which comprises (1) a step of immobilizing a ligand on a solid support via a linker cleavable by photoirradiation, (2) a step of mixing a solid support with the ligand immobilized thereon, which is obtained in the above-mentioned (1), and a sample wherein a target molecule of the ligand is contained, (3) a step of cleaving a ligand from the solid support by irradiation of light, and (4) a step of recovering the target molecule bound to the ligand.

[16] The method of the above-mentioned [15], wherein the solid support with a ligand immobilized thereon is represented by the following formula (I) or (II):

wherein X is a ligand, which is cleavable by photoirradiation; Y is a single bond or an optionally substituted alkylene group; A is a group usable for binding to a solid support; Z is a solid support; Q is NH, O or S; $R_1$ is a hydrogen atom, an optionally substituted alkyl group or an optionally substituted aryl group; $R_2$ is a hydrogen atom, an optionally substituted alkyl group, an optionally substituted aryl group, an optionally substituted alkoxy group, a halogen atom or a cyano group; $R_3$ is a hydrogen atom, an optionally substituted alkyl group, an optionally substituted aryl group, an optionally substituted alkoxy group, a halogen atom or a cyano group; $R_4$ is a hydrogen atom, an optionally substituted alkyl group, an optionally substituted aryl group, an optionally substituted alkoxy group, a halogen atom or a cyano group; and $R_5$ is a hydrogen atom, an optionally substituted alkyl group, an optionally substituted aryl group, an optionally substituted alkoxy group, a halogen atom or a cyano group.

[17] The method of the above-mentioned [16], wherein $R_2$ is a hydrogen atom, an optionally substituted alkyl group or an optionally substituted alkoxy group; $R_3$ is a hydrogen atom, an optionally substituted alkyl group or an optionally substituted alkoxy group; $R_4$ is a hydrogen atom, an optionally substituted alkyl group or an optionally substituted alkoxy group; and $R_5$ is a hydrogen atom, an optionally substituted alkyl group or an optionally substituted alkoxy group.

[18] The method of the above-mentioned [16], wherein the solid support is represented by the following formula:

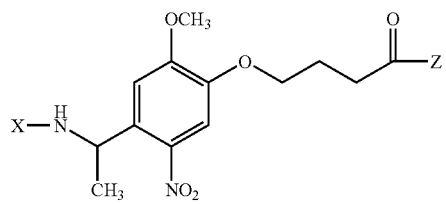

wherein each symbol is as defined above.

DETAILED DESCRIPTION OF THE INVENTION

Figure 1:
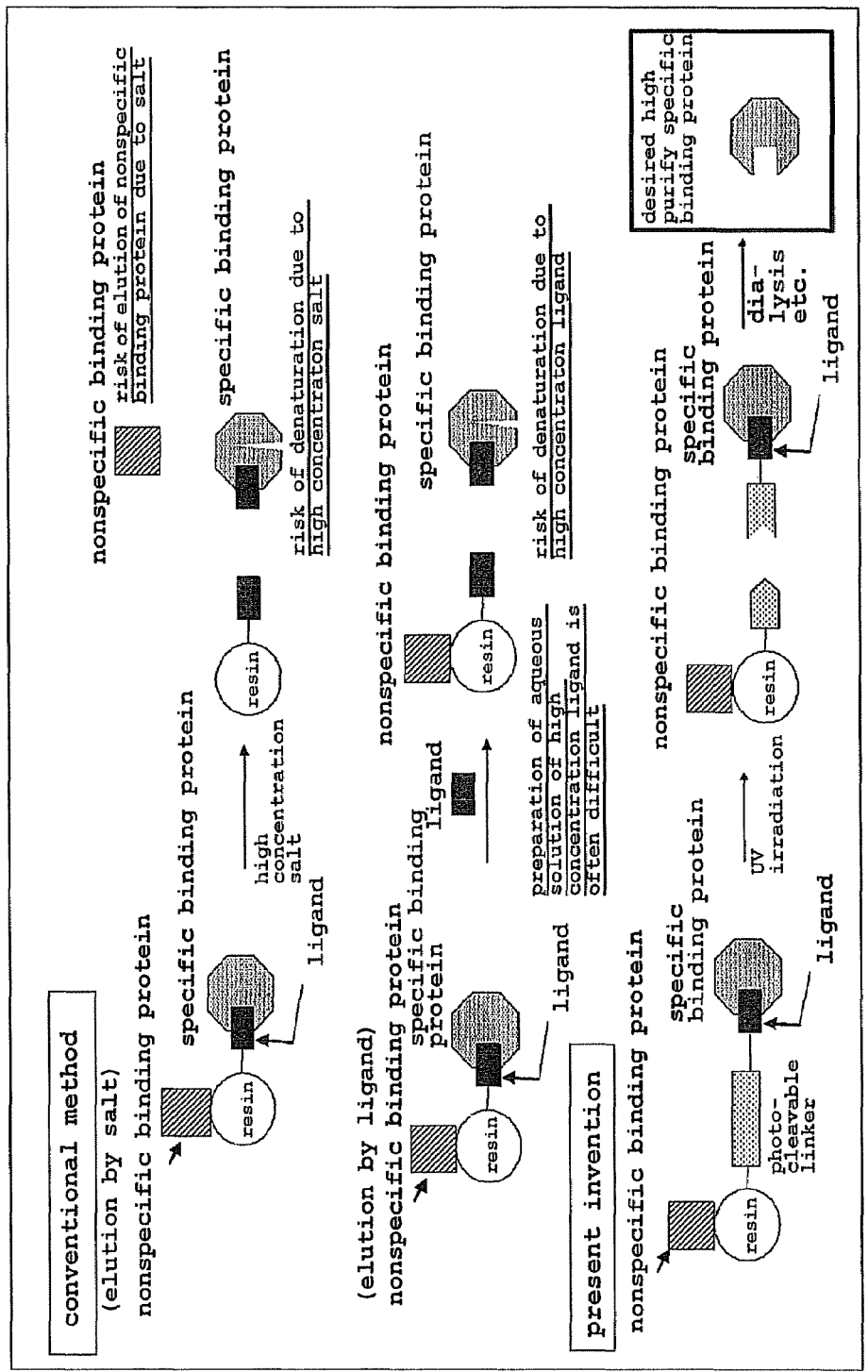
FIG. 1 is a schematic showing of a comparison of the present invention characteristically comprising immobilizing a ligand on a solid support via a photocleavable linker, and cleaving the ligand from the solid support by photoirradiation, and a conventional method comprising eluting a ligand from a solid support by adjusting a high concentration ligand or salt concentration.

The solid support of the present invention using a photocleavable linker and a method of searching and purifying a target molecule utilizing the solid support are schematically shown in FIG. 1 by comparison to a conventional method (elution method with a high concentration ligand or salt).

In the present invention, the "linker cleavable by photoirradiation" is not particularly limited as long as it can be cleaved by irradiation of the light, and is a compound (or group) that connects a ligand with a solid support (hereinafter to be also referred to as a photocleavable linker). For example, an o-nitrobenzyl linker (JOC 1995, 60, 2318-2319) used for combinatorial synthesis and various derivatives having a nitrobenzyl group can be mentioned.

As a linker cleavable by photoirradiation, a compound represented by the following formula (I') or (II') is also preferable.

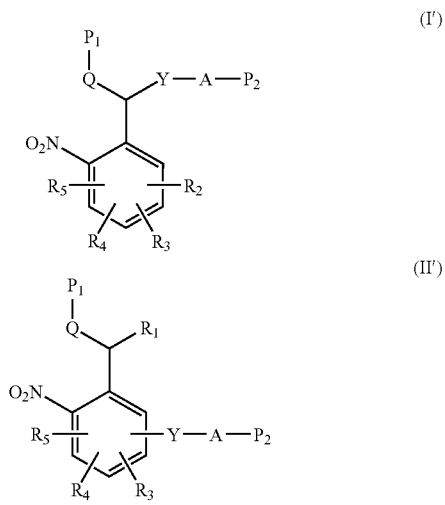

wherein $P_1$ is a hydrogen atom, or an amino-, hydroxyl- or sulfhydryl-protecting group; Y is a single bond or an optionally substituted alkylene group; A is a group usable for binding to a solid support; $P_2$ is a hydrogen atom, or an amino-, hydroxyl-, sulfhydryl-, carbonyl- or carboxyl-protecting group; Q is NH, O or S; $R_1$ is a hydrogen atom, an optionally substituted alkyl group or an optionally substituted aryl group; $R_2$ is a hydrogen atom, an optionally substituted alkyl group, an optionally substituted aryl group, an optionally substituted alkoxy group, a halogen atom or a cyano group; $R_3$ is a hydrogen atom, an optionally substituted alkyl group, an optionally substituted aryl group, an optionally substituted alkoxy group, a halogen atom or a cyano group; $R_4$ is a hydrogen atom, an optionally substituted alkyl group, an optionally substituted aryl group, an optionally substituted alkoxy group, a halogen atom or a cyano group; and $R_5$ is a hydrogen atom, an optionally substituted alkyl group, an optionally substituted aryl group, an optionally substituted alkoxy group, a halogen atom or a cyano group.

The position of the photocleavable linker, at which it is cleaved by photoirradiation, is a binding site of a linker and a ligand, and varies depending on the linker to be used and the binding manner of the linker and the ligand. For example, in a solid support represented by the below-mentioned formula (I) or (II), the Q-X bond is cleaved by photoirradiation.

The source and amount of the light to be irradiated on the linker are appropriately considered and determined depending on the kind of the linker, so that the ligand can be released. When an o-nitrobenzyl linker is used, near ultraviolet rays at a wavelength of 300-400 nm, preferably 350-370 nm, is irradiated at 0-40° C., preferably 4-25° C., for a few seconds-3 hr, preferably a few seconds-1 hr, particularly preferably 30 seconds-1 hr.

When the linker is to be cleaved by light, a suitable additive can be used, depending on the kind of the linker to be used, to prevent reaction again between a product obtained by cleavage by light and the linker. The kind and use concentration of the additive are appropriately set according to the kind of the linker to be used. When an o-nitrobenzyl linker is used, at least one kind selected from 2-mercaptoethanol, hydrazine and imidazole is preferably added. When 2-mercaptoethanol, hydrazine or imidazole is used as the additive, it is used at a concentration of 0.01-1000 mM, preferably 0.1-500 mM. When plural kinds of additives are used, the total amount is set to fall within the above-mentioned range.

While the solid support of the present invention is characterized in that the ligand is immobilized on a solid support via the above-mentioned linker, the immobilizing method is not particularly limited. A conjugate obtained by the binding of ligand and linker may be immobilized on a solid support, or a linker may be first immobilized on a solid support and the linker may be bound to a ligand.

Specifically, by dissolving the linker in an aqueous or organic solvent or a mixed solvent thereof, and mixing the thus-obtained linker solution and the solid support (solid support is also preferably suspended in an aqueous or organic solvent or a mixed solvent thereof in advance), or by subjecting the linker and the solid support to a reaction to form a covalent bond or a non-covalent bond, such as an amide bond, a bond by formation of Schiff base, a C—C bond, an ester bond, a hydrogen bond or a hydrophobic interaction, the linker is immobilized to the solid support. The aqueous or organic solvents for dissolving or suspending the linker and the solid support may be identical or not; for example, an aqueous solvent such as water or a buffer solution, and an organic solvent such as an alcohol (methanol, ethanol, and the like), dimethylformamide, dichloromethane or acetonitrile, can be mentioned. A mixed solvent thereof can also be used preferably. The reaction used to immobilize the linker to the solid support is chosen according to the kind of the functional group on the linker to be immobilized and the like, and the linker is immobilized to the solid support using an appropriately chosen known technique.

Temperatures during the series of reactions and treatments are not subject to limitation, as long as they are suitable for the immobilization reaction chosen and the linker remains stable; the reactions are normally carried out at 0° C. to 100° C., preferably at room temperature to 70° C. Time of mixing the solid support and the linker is also not subject to limitation, as long as the linker is immobilized to the solid support; this mixing time is appropriately set according to the immobilization reaction chosen; the linker to be immobilized, the kind of solid support used, and the like. That reaction time is normally 1 hour to several days, preferably 2 hours to overnight. In the binding reaction, the amount of the linker appropriately chosen according to the immobilization reaction used is generally in excess for the solid support, but not all bindable sites on the solid support or of the linker need to be subjected to the reaction. The linker need not always be in excess because the object of the present invention can be accomplished even if the linker is partially immobilized to the solid support.

The reaction used to immobilize the linker on the solid support by forming an amide bond, a Schiff base, a C—C bond, an ester bond, a hydrogen bond, a hydrophobic interaction or the like, is a technique known in the art, and can be carried out in accordance with conventional methods in terms of reaction reagents, reaction conditions and the like, which may be changed as appropriate if necessary.

Specific examples of a solid support wherein a ligand is immobilized via a photocleavable linker are given in the following with the name of the reference. Use of any of the solid supports for the analysis of interaction between a ligand and a target, or search or purification of a target molecule is not known. These solid supports can be produced by appropriately combining known literatures or known techniques. The part corresponding to the linker is conveniently encircled.

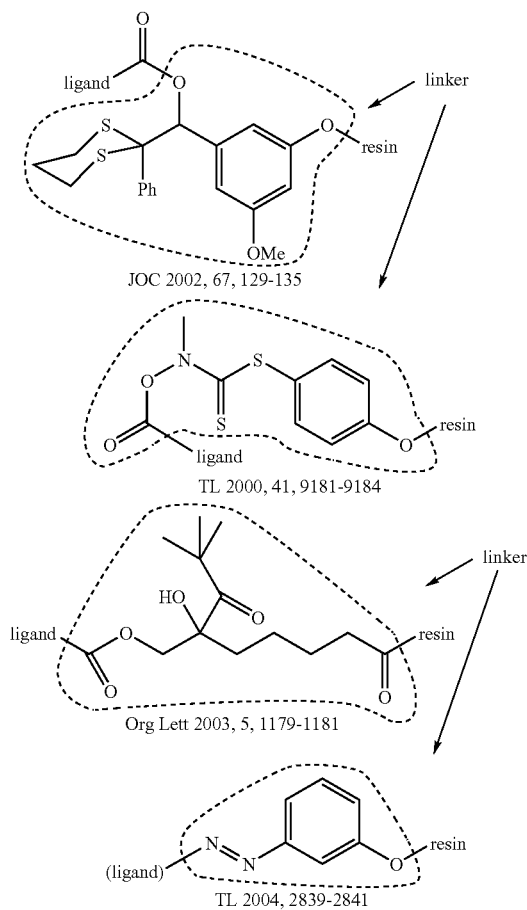

Solid supports of the following formulas (I) and (II) wherein a ligand is immobilized via a linker having a nitrobenzyl group are also preferable.

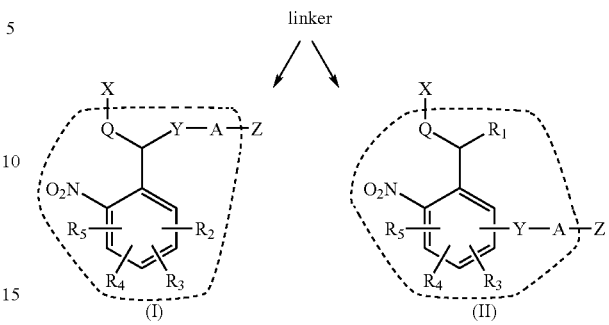

wherein X is a ligand, which is cleavable by photoirradiation; Y is a single bond or an optionally substituted alkylene group; A is a group usable for binding to a solid support; Z is a solid support; Q is NH, O or S; $R_1$ is a hydrogen atom, an optionally substituted alkyl group or an optionally substituted aryl group; $R_2$ is a hydrogen atom, an optionally substituted alkyl group, an optionally substituted aryl group, an optionally substituted alkoxy group, a halogen atom or a cyano group; $R_3$ is a hydrogen atom, an optionally substituted alkyl group, an optionally substituted aryl group, an optionally substituted alkoxy group, a halogen atom or a cyano group; $R_4$ is a hydrogen atom, an optionally substituted alkyl group, an optionally substituted aryl group, an optionally substituted alkoxy group, a halogen atom or a cyano group; and $R_5$ is a hydrogen atom, an optionally substituted alkyl group, an optionally substituted aryl group, an optionally substituted alkoxy group, a halogen atom or a cyano group.

In the formula, the solid support Z means a solid support before binding with a linker or a ligand.

The compounds of the formula (I') and the formula (II') can be synthesized, for example, by the method described in a reference (J. Org. Chem 1995, 60, 2318-2319). To be specific, group (Q) to which a ligand can bound, a nitro group, and group (A) usable for binding to a solid support are introduced into a benzene derivative bound with an alkyl group. The order of introduction of these substituents and the introductory reaction to be employed are not particularly limited, and appropriately set according to the structure of the linker to be synthesized. A conventionally-known substituent introductory reaction, for example, the reaction described in Advanced Organic Chemistry (Jerry March, 1992, John Wiley & Sons) and the like can be used.

Compounds (I') and (II') obtained by the above-mentioned method can be used as a linker used for immobilizing a ligand on a solid support, preferably a linker cleavable by photoirradiation. By immobilizing a ligand on a solid support via the linker, the solid supports (I) and (II) of the present invention can be obtained.

In the present invention, the "ligand" to be immobilized on a solid support via a photocleavable linker, for example, X in the solid supports represented by the formula (I) and the formula (II) are not subject to limitation, and may be a known compound or a novel compound that will be developed in the future. In addition, it may be a low-molecular compound or a high-molecular compound. Here, a low-molecular compound refers to a compound having a molecular weight of about less than 1000; for example, an organic compound commonly usable as a pharmaceutical, a derivative thereof, and an inorganic compound can be mentioned; specifically, a compound produced by making use of a method of organic synthesis and the like, a derivative thereof, a naturally occurring compound, a derivative thereof, a small nucleic acid molecule such as a promoter, various metals, and the like can be mentioned; and desirably, an organic compound usable as a pharmaceutical, a derivative thereof, and a nucleic acid molecule can be referred to. Also, as the high-molecular compound, a compound having a molecular weight of about 1000 or more, which is a protein, a polynucleic acid or a polysaccharide, and a combination thereof, and the like can be mentioned, and preferable is protein. These low-molecular compounds or high-molecular compounds are commercially available if they are known compounds, or can be prepared via steps such as of collection, production and purification according to various publications. These may be of natural origin, or may be prepared by gene engineering, or may be obtained by semi-synthesis and the like.

The binding of a ligand and a linker is a covalent binding or a noncovalent binding, such as amide bond, Schiff base, C—C bond, ester bond, hydrogen bond, hydrophobic interaction and the like, all of which can be formed using the material and reaction known in the pertinent field. In the case of a solid support represented by the formula (I) or the formula (II), the ligand is bound by an amide bond, thioamide bond or ester bond to NH, S or O of the linker part.

The solid support to be used in the present invention and the solid support Z in the formula (I) and the formula (II) are not particularly limited as long as the specific interaction between a ligand (immobilized on the solid support via a linker) and a target molecule occurs thereon, and those generally used in this field can be utilized. As the material, for example, resin (polystyrene, methacrylate resin, polyacrylamide etc.), glass, metal (gold, silver, iron, silicone etc.) and the like can be used. These solid phases may have any shape and are appropriately determined according to the kind of the above-mentioned material, and the method utilized thereafter for the step of analysis of the interaction with a target molecule, or search or purification of a target molecule. For example, plate, beads, thin film, yarn, coil and the like can be mentioned. Resin beads packed in a column makes the subsequent operation convenient. It is also preferable to use a glass plate.

The "group usable for binding to a solid support" for A is a joining group necessary for binding a linker part having a nitrobenzyl group (photocleavable linker) to a solid support (Z) and, for example, groups such as O, S, NH, carbonyl group and the like can be mentioned, which optionally have a combination of two or more of these groups via an alkylene group and the like (e.g., —O—(CH$_2$)$_3$—CO— etc.), or a repeat structure such as polyethylene glycol (e.g., —O—(CH$_2$CH$_2$—O)$_4$—CH$_2$CH$_2$—CO— etc.). As the bond between the "group usable for binding to a solid support" for A and a solid support (Z), amide bond, thioamide bond, carbamate bond, urea bond, thiocarbamate bond and thiourea bond of amino group on a solid support and A, amide bond and ester bond of carboxyl group on a solid support and A, ester bond and ether bond of hydroxyl group on a solid support and A, and the like can be mentioned. Any of them can be formed using the material and reaction known in this field.

In the present specification, as the halogen atom, fluorine, chlorine, bromine, iodine and the like can be mentioned.

In the present specification, the "optionally substituted alkyl group" means a linear or branched alkyl group having 1 to 3 carbon atoms, which optionally has one or more substituents. As the "linear or branched alkyl group having 1 to 3 carbon atoms", methyl, ethyl, propyl, isopropyl and the like can be specifically mentioned. As the substituent, halogen atom, (as defined above), hydroxyl group, alkoxy group (linear, branched or cyclic alkoxy group having 1 to 6 carbon atoms) and the like can be mentioned, and as the substituted alkyl group, for example, trifluoromethyl, 2-hydroxyethyl, 2-methoxyethyl and the like can be mentioned.

In the present specification, the "optionally substituted aryl group" means an aryl group having 6 to 14 carbon atoms, which optionally has one or more substituents. As the "aryl group having 6 to 14 carbon atoms", phenyl, 1-naphthyl, 2-naphthyl, 2-indenyl, 2-anthryl and the like can be specifically mentioned. As the substituent, nitro group, halogen atom (as defined above), alkyl group (linear or branched alkyl group having 1 to 3 carbon atoms), alkoxy group (as defined above) and the like can be mentioned, and as the substituted aryl group, 2-nitrophenyl, 2-chlorophenyl, 2,4-dimethoxyphenyl and the like can be mentioned.

In the present specification, the "optionally substituted alkoxy group" means a linear, branched or cyclic alkoxy group having 1 to 6 carbon atoms, which optionally has one or more substituents. As the "linear, branched or cyclic alkoxy group having 1 to 6 carbon atoms", methoxy, ethoxy, n-propoxy, isopropoxy, butoxy, isobutoxy, sec-butoxy, tert-butoxy, pentyloxy, hexyloxy, cyclopropyloxy, cyclobutyloxy and the like can be specifically mentioned. As the substituent, halogen atom (as defined above), hydroxyl group, alkoxy group (as defined above), polyethylene glycol group and the like can be mentioned, and as the substituted alkoxy group, trifluoromethoxy, 2-hydroxymethoxy, 2-methoxyethoxy, polyethylene glycol oxy and the like can be mentioned.

In the present specification, the "optionally substituted alkylene group" means a linear or branched alkylene group having 1 to 3 carbon atoms. As the "linear or branched alkylene group having 1 to 3 carbon atoms", methylene, ethylene, propylene, isopropylene and the like can be specifically mentioned. As the substituent, halogen atom (as defined above), hydroxyl group, alkoxy group (as defined above) and the like can be mentioned.

Y is preferably a single bond, A is preferably —O—(CH$_2$)$_3$—CO—, Q is preferably NH, R$_1$ is preferably optionally substituted alkyl group (particularly preferably methyl group), and R$_2$-R$_5$ are preferably hydrogen atom, optionally substituted alkyl group (particularly preferably methyl group) or optionally substituted alkoxy group (particularly preferably methoxy group).

In the present specification, the "amino-, hydroxyl- or sulfhydryl-protecting group" for P$_1$ and the "amino-, hydroxyl-, sulfhydryl-, carbonyl- or carboxyl-protecting group" for P$_2$, those generally used in this field can be utilized, and generally-used protecting groups as described in "Protective Groups in Organic Synthesis, Green and Wuts, John Wiley & Sons, Inc. 1999" and the like can be utilized. Specifically, as the "amino-protecting group", 9-fluorenylmethyloxycarbonyl, tert-butyloxycarbonyl and the like can be mentioned, as the "hydroxyl-protecting group", trityl, tert-butyl, benzyl and the like can be mentioned and, as the "sulfhydryl-protecting group", benzyl, trityl, acetamidemethyl and the like can be mentioned. The "carboxyl-protecting group" is an alkyl group (as defined above, preferably methyl, tert-butyl), aralkyl group (which has 7 to 10 carbon atoms, specifically, benzyl, methylbenzyl, phenethyl and the like, preferably, benzyl group) and the like can be mentioned. When the "group usable for binding to a solid support" for A is a carbonyl group, P$_2$ is a carbonyl-protecting group, which forms dimethylacetal, which is a carbonyl-protecting group, together with A.

A particularly preferable solid support is one represented by the formula (II) and, for example, a solid support represented by the following formula is preferable.

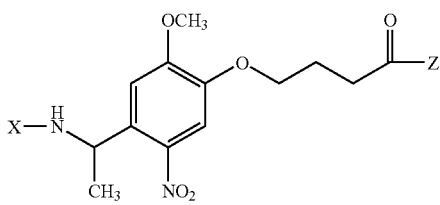

wherein each symbol is as defined above.

The solid support can be prepared by immobilizing a ligand (X) on a solid support (Z) via an o-nitrobenzyl linker represented by the following formula. Specific procedures are described below in the Examples.

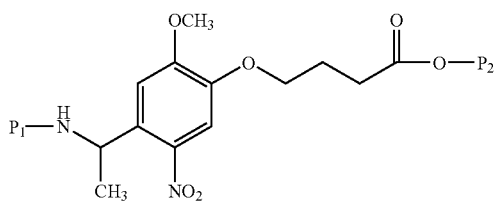

wherein each symbol is as defined above.

The present invention requires a process for searching or purifying a target molecule on the above-mentioned solid support having ligand immobilized thereon, based on the specific interaction with the ligand. Accordingly, the target molecule is not subject to limitation, as long as it specifically interacts with the ligand, and is expected to be a known compound in some cases or a novel substance in other cases. The target molecule may be a low-molecular compound or a high-molecular compound. When the target molecule is a low-molecular compound, the target molecule can be selected on the basis of the specific interaction of low-molecular compound and low-molecular compound with the ligand that is a low-molecular compound, or on the basis of the specific interaction of high-molecular compound and low-molecular compound with the ligand that is a high-molecular compound. Also, when the target molecule is a high-molecular compound, the target molecule can be selected on the basis of the specific interaction of low-molecular compound and high-molecular compound with the ligand that is a low-molecular compound, or on the basis of the specific interaction of high-molecular compound and high-molecular compound with the ligand that is a high-molecular compound. A preferable combination of the ligand and the target molecule is the combination of a low-molecular compound and a high-molecular compound, or the combination of a high-molecular compound and a high-molecular compound.

Analysis of the interaction with the target molecule and selection of the target molecule are conveniently conducted on the solid phase. When a candidate substance is anticipated as the target molecule, it is possible to bring the candidate substance alone into contact with the ligand immobilized on the solid support, assay the interaction therebetween, and determine whether or not the candidate substance is a target molecule; usually, by bringing a sample containing a plurality of substances (high-molecular compounds and/or low-molecular compounds) into contact with the ligand, and assaying the presence or absence of an interaction of each of the plurality of substances (high-molecular compounds and/or low-molecular compounds) and the ligand, and the extent of the interaction, whether or not the candidate substance is the target molecule is determined for selection. Here, the sample containing a plurality of substances may consist essentially of known compounds, may contain some novel compounds, and may consist essentially of novel compounds. However, from the viewpoint of search of target molecules for ligands, or the recent advances in proteome analysis, it is desirable that the sample be a mixture essentially of compounds of known structures. As the sample consisting essentially of known compounds, a mixture of proteins prepared by gene engineering using *Escherichia coli* and the like, and the like can be mentioned; as the sample containing some novel compounds, a cell or tissue extract (lysate) can be mentioned; as the sample that consists essentially of novel compounds, a mixture of novel proteins whose functions and structures are yet unknown, or newly synthesized compounds and the like, can be mentioned. When the sample is a mixture, especially containing known compounds, the contents of these compounds in the sample may optionally be set at desired levels in advance. From the viewpoint of search of target molecules for ligands, the target molecule to be selected is preferably a low-molecular compound or a high-molecular compound, and for search of a target molecule in the body of an animal such as a human, the target molecule is preferably a high-molecular compound.

In the present specification, the terms, ligand and target molecule, are intended to mean a combination of those having a specific intermolecular interaction with each other and, in the combination, when one is immobilized as a ligand on a solid phase, the other becomes a target molecule, where their names can be exchanged depending on which is immobilized on a solid phase. A target molecule showing a specific interaction with a ligand may not be only one kind and, similarly, a ligand showing a specific interaction with a target molecule may not be only one kind. In the present specification, the terms, ligand and target molecule, do not indicate a particular molecule, but mean each of molecules showing a specific interaction.

The "specific interaction" means an action to specifically recognize and bind to a particular ligand (particular target molecule) alone, and the relationship between specific receptor and agonist or antagonist, enzyme and substrate and, for example, FK506 (ligand) and FK506 binding protein (target molecule), steroid hormone and steroid hormone receptor (e.g., dexamethasone and glucocorticoid receptor), anticancer agent trapoxin and HDAC and the like are the "specific interaction". On the other hand, the "non-specific interaction" means an action wherein the binding targets vary widely and are not limited to a particular molecule but variously change depending on the reaction conditions, which is, in the present invention, an action between unspecified molecules that bind or adsorb to a ligand on a solid phase or the surface of the solid support itself. The "non-specific interaction" may prevent binding of ligand and target molecule based on a "specific interaction", or may be confused with the binding to overlook binding by a "specific interaction".

In the present invention, "analysis of specific interaction" means obtaining the level of specificity of the interaction between ligand and target molecule as interaction information, for example, as a numerical value such as Kd (dissociation rate constant), Ka (association rate constant) and the like. The solid support of the present invention capable of identifying a target molecule by determining the presence or otherwise of a specific interaction with a ligand based on the above-mentioned interaction information can be used for searching a target molecule. It is also possible to purify a target molecule using the solid support of the present invention, by utilizing the specific interaction between a ligand and a target molecule.

EXAMPLES

The present invention is explained in more detail in the following by referring to Examples, which are not to be construed as limitative. Unless otherwise specified, the respective compounds, reagents and the like to be used are commercially available or can be prepared based on known reports and the like.

List of Abbreviations
DMF: dimethylformamide
NMP: N-methyl-2-pyrrolidone
EDC: 1-[3-(dimethylamino)propyl]-3-ethylcarbodiimide
Fmoc: 9-fluorenylmethyloxycarbonyl
HoBt: 1-hydroxybenzotriazole
2-ME: 2-mercaptoethanol Example 1

Synthesis of Resin on which FK506 is Immobilized via a Photocleavable Linker

A mixture of a photocleavable linker (4-{4-[1-(Fmoc-amino)-ethyl]-2-methoxy-5-nitrophenoxy}butyric acid, Fluka) (124 mg, 0.24 mmol), TOYOPEARL resin (TSKgel AF-amino, 600 µl, free amino group (available amino group) was 0.06 mmol), EDC (44 mg, 0.28 mmol), HOBt (39 mg, 0.28 mmol) and DMF (6 ml) was stirred at room temperature for 15 hr. The reaction end point was confirmed by the incapability of visual observation of residual amino group in the ninhydrin reaction. The reaction rate at that time was calculated to be about 88%. After confirmation of the completion of reaction, the resin was washed 5 times with DMF. Thereto was added 20% piperidine-DMF solution (6 ml) and the mixture was stirred at room temperature for 2 hr. The resin was washed 5 times with DMF, and 200 µl thereof was taken and stirred with a mixture of 17-allyl-1,14-dihydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone (FK506; 77 mg, 0.08 mmol) prepared according to the method described in a reference (Bioconjugate Chemistry, 2003, 14(6), 1222-1230), EDC (14.9 mg, 0.096 mmol), HOBt (12.8 mg, 0.096 mmol) and DMF (1 ml) at room temperature for 20 hours. The reaction end point was confirmed by the incapability of visual observation of residual amino group in the ninhydrin reaction. The reaction rate at that time was calculated to be about 94%. After confirmation of the completion of reaction, the resin was washed 5 times with DMF. Acetic anhydride (200 µl) and DMF (800 µl) were added thereto, and this was followed by stirring at room temperature for 1 hour. Subsequently, the resin was thoroughly washed with DMF, and the obtained resin immobilizing FK506 via photocleavable linker was used for the binding assay described below.

Example 2

(1) Preparation of Rat Brain Lysate
The rat brain (2.2 g) was mixed in a mixture A (0.25M sucrose, 25 mM Tris buffer (pH 7.4), 22 ml) and prepared as a homogenate, which was then centrifuged at 9500 rpm for 10 minutes. The centrifugal supernatant was collected and further centrifuged at 50000 rpm for 30 minutes. The supernatant thus obtained was used as the lysate. Note that the experiment was entirely conducted at 4° C. or on ice.

(2) Binding Assay and Purification of Target Protein
A resin (TOYOPEARL AF) on which FK506 was immobilized via a photocleavable linker (4-{4-[1-(Fmoc-amino)-ethyl]-2-methoxy-5-nitrophenoxy}butyric acid, Fluka), which was prepared in Example 1, was mixed with a rat brain lysate prepared in the above-mentioned (1), and the attached product was washed with buffer B (25 mM tris buffer (pH 7.4), 0.25 M sucrose, 500 mM hydrazine, 500 mM 2-ME). For elution thereafter, the resin was subjected to photoirradiation in buffer B for 1 hr using a large UV irradiation lamp (365 nm, Model B100AP, Long Wave Ultraviolet Lamp, 115V-2.5A, UVP, Upland, Calif.). After the irradiation, the buffer solution was recovered as a sample, and the residual protein on the resin was eluted with an elution reagent (Sample Buffer Solution with 2ME (×2) for SDS-page, code 30566-22, Nakalai Tesuque). The sample obtained by elution of the residual protein on the resin and the sample obtained by elution by photoirradiation were compared by electrophoresis (FIG. 2).

Figure 2:
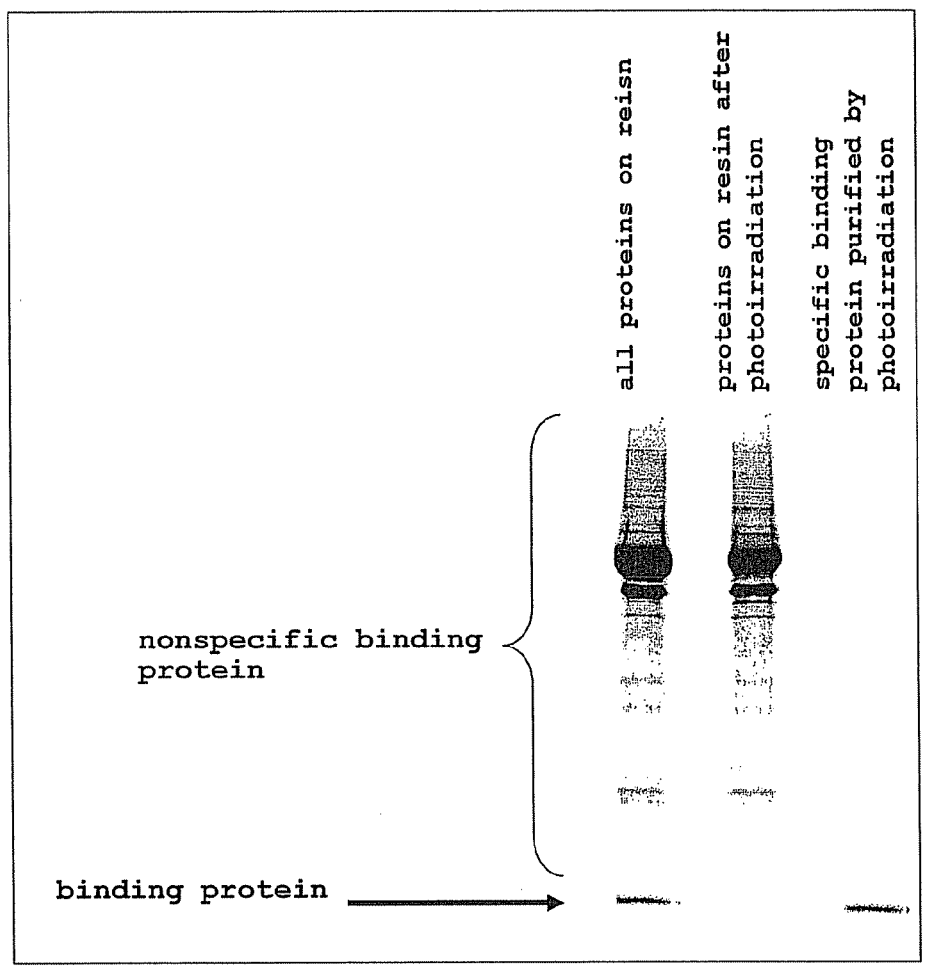
FIG. 2 shows that FK506 can be immobilized on a solid support via a photocleavable linker, and an FK506 specific binding protein FKBP12 can be obtained at a high purity from a rat brain lysate.

In the elution by photoirradiation, elution of FKBP12, which is an FK506 binding protein, at high purity from a resin, on which FK506 was immobilized via a photocleavable linker, was confirmed (FIG. 2 lane 3). When the protein on the resin after photoirradiation was eluted using an elution reagent, proteins including a nonselective binding protein other than FKBP12 were eluted (FIG. 2 lane 2). On the other hand, the results of complete elution of a protein bound to the original FK506 immobilizing resin without photoirradiation are shown in FIG. 2 lane 1.

From these results, it is clear that a specific binding protein alone is purified at a high purity according to the present invention.

Example 3

Synthesis of Resin on which Cromoglycic acid is Immobilized via a Photocleavable Linker A mixture of a resin (500 µl), on which a photocleavable linker was bound, which was prepared by the method described in Example 1, cromoglycic acid (93 mg, 0.2 mmol), EDC (37 mg, 0.24 mmol), HOBt (32 mg, 0.24 mmol) and NMP (5 ml) was stirred at room temperature for 20 hr. The reaction end point was confirmed by the incapability of visual observation of residual amino group in the ninhydrin reaction. The reaction rate at that time was calculated to be about 76%. After confirmation of completion of the reaction, the resin was washed 5 times with NMP. Acetic anhydride (1 ml) and NMP (4 ml) were added thereto, and the mixture was stirred at room temperature for 1 hour. Subsequently, the resin was thoroughly washed with NMP, and the obtained resin immobilizing cromoglycic acid via photocleavable linker was used for the binding assay described below.

Example 4

(1) Preparation of E. coli Lysate
E. coli (0.52 g) that expressed a cromoglycic acid binding protein according to a conventional method was mixed with mixture C (0.25M sucrose, 25 mM Tris buffer (pH 7.4), 1% Chaps, 4 ml), and prepared as a homogenate, which was then centrifuged at 10000 rpm for 60 minutes. The thus-obtained supernatant was used as a lysate. Note that the experiment was entirely conducted at 4° C. or on ice.

(2) Binding Assay and Purification of Target Protein

A resin (TOYOPEARL AF) on which cromoglycic acid was immobilized via a photocleavable linker (4-{4-[1-(Fmoc-amino)-ethyl]-2-methoxy-5-nitrophenoxy}butyric acid, Fluka), which was prepared in Example 3, was mixed with a cromoglycic acid binding protein expression *E. coli* lysate prepared in the above-mentioned (1), and the attached product was washed with buffer D (25 mM tris buffer (pH 7.4), 0.25 M sucrose, 1% Chaps, 500 mM imidazole, 500 mM 2-ME). For elution thereafter, the resin was subjected to photoirradiation in buffer D for 1 hr using a large UV irradiation lamp (365 nm, Model B100AP, Long Wave Ultraviolet Lamp, 115V-2.5 A, UVP, Upland, Calif.). After the irradiation, the buffer solution was recovered as a sample to give a high purity cromoglycic acid binding protein (molecular weight: about 80K) solution.

INDUSTRIAL APPLICABILITY

According to the method of the present invention, denaturation of protein due to high concentration ligand or salt, contamination with a nonselective protein and the like, which have been problematic in conventional purification process of protein by an affinity resin with an immobilized ligand having a specific binding ability, can be obliterated.

This application is based on a patent application No. 2004-224634 filed in Japan, the contents of which are incorporated in full herein by this reference.

The invention claimed is:

1. A method of searching a target molecule, which comprises
   (1) immobilizing a ligand on a solid support via a linker cleavable by photoirradiation,
   (2) mixing a solid support with the ligand immobilized thereon, which is obtained in the above-mentioned (1), and a sample wherein a target molecule of the ligand is or is not contained,
   (3) cleaving a ligand from the solid support by irradiation of light in the presence of 2-mercaptoethanol and/or hydrazine, and
   (4) confirming binding of the target molecule to the ligand.

2. The method of claim 1, wherein the solid support with a ligand immobilized thereon is represented by the following formula (I) or (II):

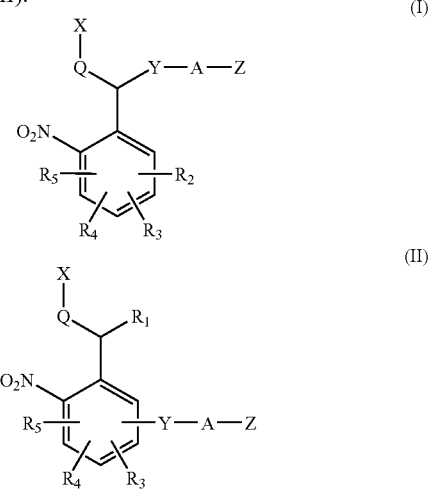

wherein
X is a ligand, which is cleavable by photoirradiation;
Y is a single bond or an optionally substituted alkylene group;
A is a group usable for binding to a solid support;
Z is a solid support; Q is NH, O or S;
$R_1$ is a hydrogen atom, an optionally substituted alkyl group or an optionally substituted aryl group;
$R_2$ is a hydrogen atom, an optionally substituted alkyl group, an optionally substituted aryl group, an optionally substituted alkoxy group, a halogen atom or a cyano group;
$R_3$ is a hydrogen atom, an optionally substituted alkyl group, an optionally substituted aryl group, an optionally substituted alkoxy group, a halogen atom or a cyano group;
$R_4$ is a hydrogen atom, an optionally substituted alkyl group, an optionally substituted aryl group, an optionally substituted alkoxy group, a halogen atom or a cyano group; and
$R_5$ is a hydrogen atom, an optionally substituted alkyl group, an optionally substituted aryl group, an optionally substituted alkoxy group, a halogen atom or a cyano group.

3. The method of claim 2, wherein
$R_2$ is a hydrogen atom, an optionally substituted alkyl group or a optionally substituted alkoxy group;
$R_3$ is a hydrogen atom, an optionally substituted alkyl group or an optionally substituted alkoxy group;
$R_4$ is a hydrogen atom, an optionally substituted alkyl group or an optionally substituted alkoxy group; and
$R_5$ is a hydrogen atom, an optionally substituted alkyl group or an optionally substituted alkoxy group.

4. The method of claim 2, wherein the solid support is represented by the following formula:

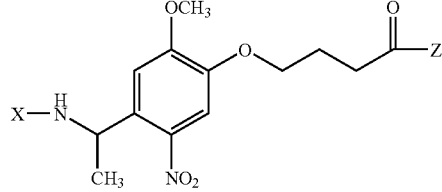

wherein each symbol is as defined above.

5. A method of purifying a target molecule, which comprises
   (1) immobilizing a ligand on a solid support via a linker cleavable by photoirradiation,
   (2) mixing a solid support with the ligand immobilized thereon, which is obtained in the above-mentioned (1), and a sample wherein a target molecule of the ligand is contained,
   (3) cleaving a ligand from the solid support by irradiation of light in the presence of 2-mercaptoethanol and/or hydrazine, and
   (4) recovering the target molecule bound to the ligand.

6. The method of claim 5, wherein the solid support with a ligand immobilized thereon is represented by the following formula (I) or (II):

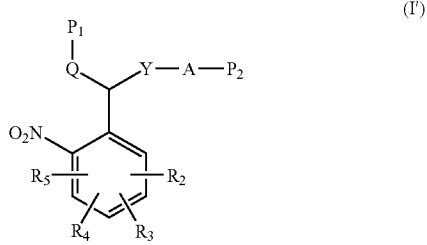

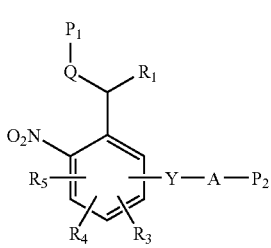

wherein

X is a ligand, which is cleavable by photoirradiation;

Y is a single bond or an optionally substituted alkylene group;

A is a group usable for binding to a solid support;

Z is a solid support;

Q is NH, O or S;

$R_1$ is a hydrogen atom, an optionally substituted alkyl group or an optionally substituted aryl group;

$R_2$ is a hydrogen atom, an optionally substituted alkyl group, an optionally substituted aryl group, an optionally substituted alkoxy group, a halogen atom or a cyano group;

$R_3$ is a hydrogen atom, an optionally substituted alkyl group, an optionally substituted aryl group, an optionally substituted alkoxy group, a halogen atom or a cyano group;

$R_4$ is a hydrogen atom, an optionally substituted alkyl group, an optionally substituted aryl group, an optionally substituted alkoxy group, a halogen atom or a cyano group; and $R_5$ is a hydrogen atom, an optionally substituted alkyl group, an optionally substituted aryl group, an optionally substituted alkoxy group, a halogen atom or a cyano group.

7. The method of claim 6, wherein $R_2$ is a hydrogen atom, an optionally substituted alkyl group or an optionally substituted alkoxy group;

$R_3$ is a hydrogen atom, an optionally substituted alkyl group or an optionally substituted alkoxy group;

$R_4$ is a hydrogen atom, an optionally substituted alkyl group or an optionally substituted alkoxy group; and $R_5$ is a hydrogen atom, an optionally substituted alkyl group or an optionally substituted alkoxy group.

8. The method of claim 6, wherein the solid support is represented by the following formula:

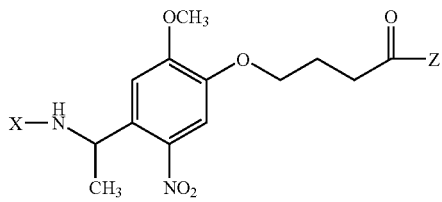

wherein each symbol is as defined above.

* * * * *

UNITED STATES PATENT AND TRADEMARK OFFICE
CERTIFICATE OF CORRECTION

PATENT NO. : 7,456,022 B2  Page 1 of 1
APPLICATION NO. : 11/572972
DATED : November 25, 2008
INVENTOR(S) : Haramura et al.

It is certified that error appears in the above-identified patent and that said Letters Patent is hereby corrected as shown below:

Col. 18-19 in claim 6, formulas (I) and (II) should read:

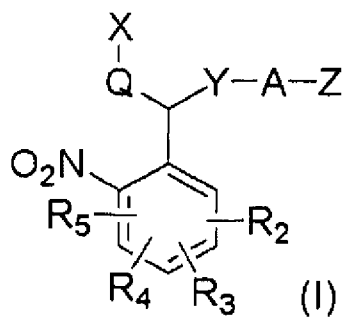
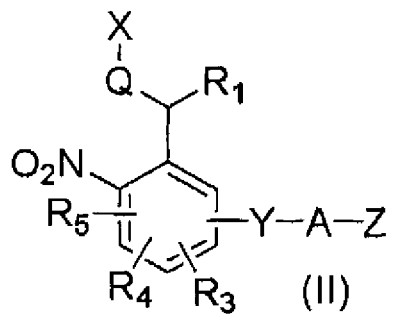

Signed and Sealed this

Twenty-fourth Day of March, 2009

JOHN DOLL
*Acting Director of the United States Patent and Trademark Office*